US007454947B2

(12) United States Patent
Roby

(10) Patent No.: US 7,454,947 B2
(45) Date of Patent: Nov. 25, 2008

(54) METHOD OF DETERMINING DIESEL ENGINE VALVE TRAIN WEAR USING A CARBON BLACK PARTICLE MIXTURE

(75) Inventor: Stephen H. Roby, Hercules, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 11/316,156

(22) Filed: Dec. 20, 2005

(65) Prior Publication Data
US 2007/0137282 A1 Jun. 21, 2007

(51) Int. Cl.
G01N 3/56 (2006.01)
G01M 15/00 (2006.01)
(52) U.S. Cl. ............... 73/7; 73/10; 73/119 R; 73/120
(58) Field of Classification Search ........ 73/7, 73/9, 10, 53.05, 53.06, 119 R, 120
See application file for complete search history.

(56) References Cited

U.S. PATENT DOCUMENTS

| 4,765,964 | A * | 8/1988 | Gravley et al. ........... 422/156 |
| 6,358,487 | B1 * | 3/2002 | Omae et al. ............. 423/450 |
| 2004/0038836 | A1 * | 2/2004 | Devlin et al. ............ 508/371 |
| 2005/0124509 | A1 * | 6/2005 | Gutierrez et al. ......... 508/291 |
| 2005/0178190 | A1 * | 8/2005 | Wollenberg ............. 73/53.01 |

FOREIGN PATENT DOCUMENTS

JP 2001 004620 A 1/2001

OTHER PUBLICATIONS

Rezikov et al., "Efficiency Criteria for Motor Oils", 1990, pp. 445-451.*

Lepperhoff, Gerhard, "Influences on the Particle Size Distribution of Diesel Particulate Emissions", Sep. 2001, Topics in Catylsts, vol. 16-17, Nos. 1-4 pp. 249-254.*
Mathis et al., "Influence of Diesel Engine Combustion Parameters on Primary Soot Particle Diameter", Feb. 2005, Environmental Science and Technology, vol. 39, No. 6, pp. 1887-1892.*
Gautam et al., Effect of Diesel Soot Contaminated Oil on Engine Wear—Investigation of Novel Oil Formulations, 1999, Tribology International, vol. 32, pp. 687-699.*
Lockwood et al., "Thermal Characteristics of New and Used Diesel Engine Oils", 2001, Proceedings of the 2nd World Tribology Congress.*
European Search Report for EP App. No. 06 25 615B, dated Oct. 23, 2007.
Bergezier et al.; "The Role of Carbon in Lubricated Mild Wear"; Tribology International; vol. 19, No. 3; Jun. 1986; pp. 115-122; XP002455244.
Gautam, et al.; "Effect of diesel soot contaminate oil on engine wear-investigation of novel oil formulations", Tribology International; vol. 32; 1999; pp. 687-699, XP002455245; pp. 689-690.
Machine Translation of JP 2001 004620A dated Jan. 2001.

* cited by examiner

Primary Examiner—Hezron Williams
Assistant Examiner—David A. Rogers
(74) Attorney, Agent, or Firm—Claude J. Caroli; Joseph P. Foley

(57) ABSTRACT

A method is described to determine the valve train wear performance of a lubricating oil by adding to the lubricating oil from about 2% to about 9% by weight, based on the total weight of the lubricating oil, of a mixture of at least three carbon black components of mixed particle size and measuring the wear induced in a wear test.

11 Claims, 2 Drawing Sheets

METHOD OF DETERMINING DIESEL ENGINE VALVE TRAIN WEAR USING A CARBON BLACK PARTICLE MIXTURE

The present invention relates to a method of determining diesel engine valve train wear. More particularly, the present invention relates to a method of determining the wear characteristics of a fully-formulated lubricating oil by adding carbon black components having mixed particle size to the lubricating oil and analyzing the lubricating oil containing the carbon black components in a wear test.

BACKGROUND OF THE INVENTION

In recent years, new environmental regulations have forced engine manufacturers to modify engine compression and timing to control soot particulate and oxides of nitrogen (NOx) emissions better. Engine manufacturers have modified their designs to improve emissions controls. Further regulations have triggered wide-spread use of exhaust emission catalyst systems, some to trap carbonaceous particulates and others to decompose NOx and hydrocarbons. The combination of engine operating conditions and emission control system changes, particularly the introduction of exhaust gas recirculation (EGR), has increased the soot loading of diesel engine lubricants. The soot particulates can be quite hard and abrasive. Consequently, the increased soot loading in modern diesel engines has contributed to higher valve train wear rates.

Since some engine manufacturers believe that phosphorus and sulfur may poison exhaust catalysts, a simultaneous trend has been the reduction of phosphorus and sulfur content of heavy duty motor oils (HDMO). Phosphorus and sulfur may poison emission control catalysts. Phosphorus comes from zinc alkyl dithiophosphate (ZnDTP), the predominant antiwear agent for the past 50 years. Sulfur, too, is present in ZnDTP and in most commercial detergents, either sulfonates or phenates. The detergents are key components of engine oils, present to neutralize acidic oxidation products and to suspend varnish and sludge deposits. In order to protect and extend the life of the emission control catalysts, engine manufacturers are requesting lubricants with ever lower phosphorus and sulfur levels. Therefore, ZnDTP and traditional sulfur-based detergents are being replaced with additives that do not contribute phosphorus or sulfur.

Reduction of the phosphorus and sulfur content while increasing the soot-loading of diesel engine oils in the field present fundamental changes in formulating strategy. A further complication is that fully-formulated lubricants are time-consuming and costly to develop. A typical engine test program for the American Petroleum Institute (API) Cl-4 specification can easily exceed $1,000,000.

Bench testing can be a cost-effective alternative to full scale engine tests. Bench tests can moderate costs by simulating valve train wear in small, inexpensive rigs. Thus, a bench test is generally inexpensive, perhaps only $100. To be of use to the formulator or additive synthesis chemist and to reduce engine test costs, the bench test must be related to a key engine test parameter. This is most often done by the careful selection of reference oils with known performance in that key engine test. In the case of a heavy duty valve train wear test, the proper selection of appropriate bench test reference fluids and surrogate soot are vital.

Ideally, a diesel wear bench test would use actual engine soot. However, engine soot is difficult to isolate from used engine oil, requiring dilution and high speed centrifugation to precipitate the soot, then further washing steps to remove residual oil and additives. The amount of isolated soot is low, less than 10% by weight of the original oil sample. The precipitated soot will contain additives or additive fragments that washing will not remove. Overall, engine soot is time-consuming to isolate and prepare, highly variable in composition (because of the engine oil additives), and available in limited quantity.

Carbon black is an attractive, practical alternative to engine soot. Carbon black is globally available in commercial quantities. Its chemical and physical properties can be selected to mimic those of the engine soot of interest. Overall, carbon black is a cost- and time-effective alternative to engine soot for bench testing applications. Thus, it is highly desirable to establish a bench test using carbon black that can reliability predict soot performance of lubricating oils.

SUMMARY OF THE INVENTION

The present invention relates a method of determining diesel engine valve train wear. More particularly, the present invention relates to a method of determining the wear characteristics of a fully-formulated lubricating oil by adding carbon black components having mixed particle size to the lubricating oil and analyzing the lubricating oil containing the carbon black components in a wear test.

Accordingly, in its broadest aspect, the present invention is related to a method to determine the valve train wear performance of a lubricating oil by adding to the lubricating oil from about 2% to about 9% by weight, based on the total weight of the lubricating oil, of a mixture of at least three carbon black components of mixed particle size and measuring the wear induced in a wear test, such as, for example, a high frequency reciprocating rig (HFRR) (PCS Instruments) test.

Preferably the amount of the mixture of carbon black components is from about 5% to about 7% by weight, based on the total weight of the lubricating oil.

The particle size of each carbon black component is independently in the range from about 10 nanometers to about 100 nanometers, preferably from about 10 nanometers to about 75 nanometers and more preferably in the range from about 15 nanometers to about 60 nanometers. Preferably, the three carbon black components have a particle size of 17 nanometers, 29 nanometers and 56 nanometers, respectively.

The mixture of carbon black components employed in the present invention is a mixture of three carbon black components. The concentration of each carbon black component in the lubricating oil will independently range from about 1.8% to about 2.2% by weight, based on the total weight of the lubricating oil. Preferably, the concentration of each of the carbon black components in the lubricating oil is about 2% by weight, based on the total weight of the lubricating oil.

The lubricating oil comprises a major amount of base oil of lubricating viscosity and a minor amount of at least one additive selected from the group consisting of detergents, dispersants, oxidation inhibitors, rust inhibitors, demulsifiers, extreme pressure agents, friction modifiers, multifunctional additives, viscosity index improvers, pour point depressants, foam inhibitors and wear inhibitors.

Among other factors, the present invention is based on the surprising discovery that a wear test, such as the HFRR test, using a mixture of at least three carbon black components of mixed particle size provides a reliable method of determining valve train performance of lubricating oils.

DETAILED DESCRIPTION OF THE INVENTION

Figure 1A:
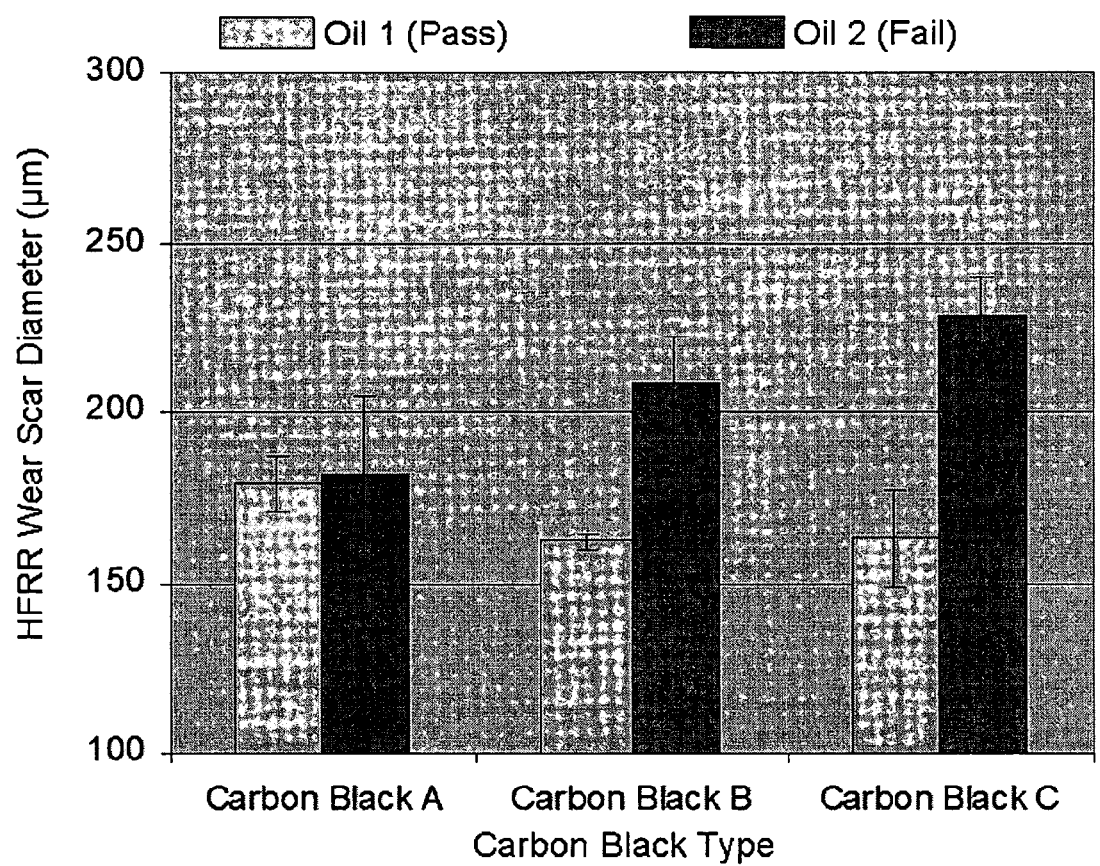
FIG. 1A illustrates the effect of particle size on HFRR wear data for single carbon blacks.

Soot particles are known to cause wear in diesel engines. In recent years, the higher soot loading of the engine oils induced by emission control systems has translated to higher valve train wear.

Studies have shown that engine soot is composed of graphite-like particles with an average diameter of about 20 to about 30 nanometers (nanometers).

The soot particles clump together to form larger aggregates. The aggregates can become quite large, on the order of 1 µm in diameter in some engines. Aggregation can be controlled by the judicious selection of dispersant type and level. In bench testing, diesel engine soot is occasionally used but is most often simulated with a carbon black. Carbon black is similar in structure to actual engine soot and is available in commercial quantities with a wide variety of chemical and physical properties.

The present invention is a method to determine the valve train wear performance of a lubricating oil by adding to the lubricating oil a mixture of carbon black components of mixed particle size and measuring the wear induced in a wear test. The amount of the mixture of carbon black components is from about 2% to about 9% by weight, based on the total weight of the lubricating oil. Preferably, the amount of the mixture of carbon black components added is from about 5% to about 7% by weight, based on the total weight of the lubricating oil.

The method of the present invention will utilize a mixture of carbon black components containing a mixture of three carbon black components. The particle size of each carbon black component is independently in the range from about 10 nanometers to about 100 nanometers, preferably from about 10 nanometers to about 75 nanometers and more preferably from about 15 nanometers to about 60 nanometers. Preferably, the three carbon black components have a particle size of 17 nanometers, 29 nanometers and 56 nanometers, respectively.

Preferably, the method of the present invention will use a mixture of carbon black components containing three carbon black components. The concentration of each carbon black component in the lubricating oil will independently range from about 1.8% to about 2.2% by weight, based on the total weight of the lubricating oil. Preferably, the concentration of each of the carbon black components in the lubricating oil is about 2% by weight, based on the total weight of the lubricating oil.

Until now, mixtures of carbon black components of mixed particle size have not been used in soot performance wear testing. It has now been discovered that having a mixture of at least three carbon black components provides better valve train wear discrimination between good and poor lubricating oils when used in the HFRR test.

The HFRR test was developed as a screen for the Cummins M11 EGR engine test. In this test, an electromagnetic vibrator is used to oscillate a specimen (the ball) over a small amplitude while pressing against a fixed specimen (a flat disk). The amplitude and frequency of the oscillation and the load are variable. The frictional force between the ball and flat and the electrical contact resistance (ECR) are measured. The flat, stationary specimen is held in a bath to which the lubricating oil is added, and can be heated.

The lubricating oils are pretreated with about 6% by weight, based on the total weight of lubricating oil, carbon black. The carbon black is stirred into the oil to wet it and then homogenized for 15 minutes prior to testing.

The wear scars on the balls are measured manually on an optical microscope and recorded. The test oil is run three times.

The lubricating oil employed in the method of the present invention is a lubricating oil comprising a major amount of a base oil of lubricating viscosity and at least one additive selected for the group consisting of detergents, dispersants, oxidation inhibitors, rust inhibitors, demulsifiers, extreme pressure agents, friction modifiers, multifunctional additives, viscosity index improvers, pour point depressants, foam inhibitors and wear inhibitors.

Base Oil of Lubricating Viscosity

Base oil as used herein is defined as a base stock or blend of base stocks which is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100° Centigrade (° C.) and about 4 centistokes (cSt) to about 20 cSt. Hydrocarbon synthetic oils may include, for example, oils prepared from the polymerization of ethylene, polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity about 20 cSt or higher at about 100° C. Oils used as the base oil will be selected or blended depending on the desired end use and the additives in the finished oil to give the desired grade of engine oil, e.g. a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, or 15W-40.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14$^{th}$ Edition, Addendum I, December 1998. Saturates levels and viscosity indices for Group I, II and III base oils are listed in Table 1. Group IV base oils are polyalphaolefins (PAO). Group V base oils include all other base oils not included in Group I, II, III, or IV. Group III base oils are preferred.

TABLE 1

SATURATES, SULFUR AND VISCOSITY INDEX OF
GROUP I, II, III, IV AND V BASE STOCKS

| Group | Saturates (As determined by ASTM D2007) Sulfur (As determined by ASTM D2270) | Viscosity Index (As determined by ASTM D4294, ASTM D4297 or ASTM D3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |
| IV | All Polyalphaolefins (PAOs) | |
| V | All others not included in Groups I, II, III, or IV | |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from about C5 to about C12 monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil.

Such wax isomerate oil is produced by the hydroisomerization of natural or synthetic waxes or mixtures thereof over a hydroisomerization catalyst.

It is preferred to use a major amount of base oil of lubricating viscosity in the lubricating oil composition of the present invention. A major amount of base oil of lubricating viscosity as defined herein comprises 40 wt % or more. Preferred amounts of base oil comprise about 40 wt % to about 97 wt %, preferably greater than about 50 wt % to about 97 wt %, more preferably about 60 wt % to about 97 wt % and most preferably about 80 wt % to about 95 wt % of the lubricating oil composition. (When weight percent is used herein, it is referring to weight percent of the lubricating oil composition unless otherwise specified.)

A minor amount of other additives commonly founded in lubricating oil compositions may be present in the lubricating oil such as described below. By minor amount, it is meant that the wt % will be less that wt % of base oil of lubricating viscosity such that the total wt % amount to 100% of the lubricating oil composition.

(A) Metal Detergents: sulfurized or unsulfurized alkyl or alkenyl phenates, alkyl or alkenyl aromatic sulfonates, calcium sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multi-acid, and chemical and physical mixtures thereof.

(B) Ashless dispersants: alkenyl succinimides, alkenyl succinimides modified with other organic compounds, e.g., ethylene carbonating post-treatment and alkenyl succinimides modified with boric acid, polysuccinimides, alkenyl succinic ester.

(C) Oxidation inhibitors:
(1) Phenol type phenolic) oxidation inhibitors: 4,4'-methylenebis (2,6-di-tert-butylphenol),4,4'-bis(2,6-di-tert-butylphenol), 4,4'-bis(2-methyl-6-tert-butylphenol), 2,2'-(methylenebis(4-methyl-6-tert-butyl-phenol), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidenebis(4,6-dimethylphenol), 2,2'-methylenebis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-α-dimethylamino-p-cresol, 2,6-di-tert-4(N,N' dimethylaminomethylphenol),4,4'-thiobis(2-methyl-6-tert-butylphenol), 2,2'-thiobis(4-methyl-6-tert-butyl phenol), bis(3-methyl-4-hydroxy-5-tert-butylbenzyl)-sulfide, and bis(3,5-di-tert-butyl-4-hydroxybenzyl).

(2) Diphenylamine type oxidation inhibitor: alkylated diphenylamine, phenyl-α-naphthylamine, and alkylated α-naphthylamine.

(3) Other types: metal dithiocarbamate (e.g., zinc dithiocarbamate), and methylenebis(dibutyidithiocarbamate).

(D) Rust inhibitors (Anti-rust agents):
(1) Nonionic polybxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

(2) Other compounds: stearic acid and other fatty acids, dicarboxilic acids, metal soaps, fatty acid amine salts, metal salts of heavy sulfonic acid, partial carboxylic acid ester of polyhydric alcohol, and phosphoric ester.

(E) Demulsifiers: addition product of alkylphenol and ethyleneoxide, polyoxyethylene alkyl ether, and polyoxyethylene sorbitane ester.

(F) Extreme pressure agents (EP agents): sulfurized oils, diphenyl sulfide, methyl trichlorostearate, chlorinated naphthalene, benzyl iodide, fluoroalkylpolysiloxane, and lead naphthenate.

(G) Friction modifiers: fatty alcohol, fatty acid, amine, borated ester, and other esters.

(H) Multifunctional additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound.

(I) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(J) Pour point depressants: polymethyl methacrylate, alkylmethacrylates, and dialkyl fumarate—vinyl acetate copolymers.

(K) Foam Inhibitors: alkyl methacrylate polymers and dimethyl silicone polymers.

(L) Wear Inhibitors: zinc dialkyldithiophosphate (Zn-DTP, primary alkyl type & secondary alkyl type).

EXAMPLES

Example 1

Formulations

Two lubricating oils (Oil 1 and Oil 2) were blended as specified in Table 2. Both were fully-formulated PC-10 prototype formulations.

TABLE 2

TEST OIL FORMULATION

| Component | Oil 1 | Oil 2 |
|---|---|---|
| Borated Succinimide | 3.02 | 3.02 |
| EC-Treated Succinimide | 5.03 | 5.03 |
| Dispersant Viscosity Index Improver | 5.03 | 0 |
| Overbased Sulfonate | 0.68 | 0.68 |
| Overbased Salicylate | 4.31 | 4.31 |
| Phosphorus Wear Inhibitor | 0.69 | 0.69 |
| Molybdenum Antioxidant | 0.40 | 0.40 |
| Oxidation Inhibitor | 0.50 | 0.50 |
| Foam Inhibitor | 0.02 | 0.02 |
| OCP Viscosity Index Improver | 2.52 | 8.06 |
| Pour Point Depressant | 0 | 0.27 |
| Group II Base Oil | 0 | 5 |
| Group III Base Oil | 77.78 | 72.0 |

Both oils were evaluated for valve train wear performance in the Cummins M-11EGR engine test. The results are summarized in Table 3.

TABLE 3

LUBRICANT FORMULATIONS AND CUMMINS M-11EGR VALVE TRAIN WEAR PERFORMANCE

| | API CI-4 Limit (mg) | Oil 1 | Oil 2 |
|---|---|---|---|
| M-11EGR Crosshead Weight Loss | 20.0 (maximum) | 19.7 | 39.7 |

Oil 1 had acceptable Cummins M-11 EGR crosshead wear (19.7 mg), whereas Oil 2 had poor M-11EGR crosshead wear (39.7 mg). The passing limit is 20 mg. Base on these results Oil 1 was designated the "good" oil and Oil 2 was designated the "poor" oil for the carbon black experiments described below.

Example 2

Carbon Black Characterization

Three commercially available carbon blacks (from Degussa Company) were selected to serve as soot surrogates. Table 4 shows the key physical characteristics of these carbon blacks.

TABLE 4

SELECTED PHYSICAL PROPERTIES OF CARBON BLACKS (INFORMATION FURNISHED BY THE SUPPLIER)

| Carbon Black | Primary particle size (nanometers) | pH | BET Surface Area |
|---|---|---|---|
| A | 17 | 4 | 200 |
| B | 29 | 4 | 90 |
| C | 56 | 3.1 | 40 |

Scanning electron microscopy of these carbon blacks indicated that the particle sizes appear remarkably consistent. The average diameter of each carbon black was in line with manufacturer specifications.

Each carbon black was analyzed by X-ray Photoelectron Spectroscopy (XPS) to examine the surface chemistry and to ensure that the carbon blacks were indeed chemically similar. The results of the XPS analyses are presented in Table 5.

TABLE 5

X-RAY PHOTOELECTRON SPECTROSCOPY ANALYSES OF THE CARBON BLACKS

| | Carbon Black | | |
|---|---|---|---|
| Elements | A | B | C |
| Particle Size (nanometers) | 17 | 29 | 56 |
| Hydrocarbon | 74.91 | 76.73 | 77.43 |
| Alcohol/Ether | 13.56 | 12.18 | 11.93 |
| Carbonyl | 5.19 | 4.91 | 4.33 |
| Carboxyl | 4.25 | 3.74 | 3.90 |
| Nitrate, nitroso | 0.01 | 0.02 | 0.16 |
| O 1 | 0.77 | 0.96 | 0.88 |
| O 2 | 1.22 | 1.31 | 1.35 |
| Sulfur | 0.07 | 0.12 | 0.02 |
| Sulfate | 0.02 | 0.05 | 0.01 |
| | 100.00 | 100.00 | 100.00 |
| C tot | 97.91 | 97.55 | 97.59 |
| C ox | 23.00 | 20.82 | 20.16 |
| C ox/C tot | 0.23 | 0.21 | 0.21 |
| N | 0.01 | 0.02 | 0.16 |
| O tot | 1.99 | 2.27 | 2.23 |
| O 1/O tot | 0.38 | 0.42 | 0.40 |
| S tot | 0.09 | 0.16 | 0.02 |
| S 1/S tot | 0.78 | 0.72 | 0.77 |

Results of the XPS indicated that the carbon blacks are very similar in chemical content, ranging from about 20% to about 23% oxidized carbon. Sulfur is somewhat higher in the smaller particular size materials. Nitrogen is a bit higher in the larger particles.

Example 3

Valve Train Wear Performance Determination

To simulate soot in a lubricating oil, about 6% carbon black by weight was added to the lubricating oils (Oil 1 and Oil 2). The carbon black as thoroughly dispersed in the lubricating oil with a homogenizer. Because of the high shear, the temperature of the lubricating oil reached approximately 80° C. The lubricating oil containing the carbon black was determined for valve train wear performance using the HFRR test.

A. Single Carbon Black Experiments

In this experiment, about 6% by weight of a single carbon black was added to Oil 1 and Oil 2 to examine the effect of particle size on HFRR valve train wear performance.

The HFRR test is an industry recognized bench test for determining the valve train wear performance in candidate lubricating oils. The PCS instrument uses an electromagnetic vibrator to oscillate a specimen (the ball) over a small amplitude while pressing against a fixed specimen (a flat disk). The amplitude and frequency of the oscillation and the load are variable. The frictional force between the ball and flat and the electrical contact resistance (ECR) are measured. The flat, stationary specimen is held in a bath to which the lubricating oil is added, and can be heated.

The lubricating oils are pretreated with about 6% by weight carbon black. The carbon black is stirred into the lubricating oil to wet it and then homogenized for about 15 minutes prior to testing.

The wear scars on the balls are measured manually on an optical microscope and recorded. The lubricating oil is run three times. The results are summarized in Table 6 and also pictorially presented in FIG. 1A.

TABLE 6

HFRR RESULTS FOR SINGLE CARBON BLACK EXPERIMENTS

| Prototype Lubricant | Carbon Black A | Carbon Black B | Carbon Black C | Wear Scar Diameter (μ) | Wear Scar Diameter Standard Deviation (μ) |
|---|---|---|---|---|---|
| Oil 1 | 6 | | | 179 | 8 |
| Oil 2 | 6 | | | 182 | 23 |
| Oil 1 | | 6 | | 162 | 2 |
| Oil 2 | | 6 | | 208 | 14 |
| Oil 1 | | | 6 | 163 | 14 |
| Oil 2 | | | 6 | 228 | 11 |

Wear for the poor oil (Oil 2) appears to increase as the carbon black particle size increases. For single carbon blacks, the maximum discrimination in HFRR wear performance occurs with about 6% by weight of carbon black C, the carbon black with the largest particle size. As the particle size increased, HFRR wear increased in the poor oil. Interestingly, wear for the good oil (Oil 1) does not change with increasing particle size.

Therefore, the discrimination between good and poor oil increases or appears to become more apparent as particle size increases. The difference between the good oil and the poor oil increased by approximately 40%. The larger particle size improves discrimination between engine oils of known wear performance.

Without limiting the present invention to theory, it is thought that soot-induced wear suggests that large particles become entrained in the contact zone and produce abrasive wear. Smaller particles are lesser in size than the oil film thickness so do not produce abrasion. Larger particles are too big to fit into the contact zone. Therefore, selecting the appropriate particle size is crucial in bench test wear determinations. These results suggest that the largest particles produce the largest wear under pure boundary conditions.

B. Carbon Black Mixture Experiments

A statistically designed mixture experiment was performed to examine the effect of particle size, and combinations of particle size, on HFRR wear performance. The total amount of carbon black in a blend was fixed at about 6% by weight. Up to three carbon black components were used in each blend. Both good and poor oils were tested. The run order of the mixtures was randomized to minimize bias. The results are presented in Table 7 and pictorially in FIG. 1B.

TABLE 7

CARBON BLACK MIXTURE STUDY HFRR WEAR DATA

| Prototype Lubricant | Carbon Black A | Carbon Black B | Carbon Black C | Wear Scar Diameter (μ) | Wear Scar Diameter Standard Deviation (μ) |
|---|---|---|---|---|---|
| Oil 1 | 3 | 3 | | 170 | 16 |
| Oil 1 | | 3 | 3 | 165 | 15 |
| Oil 1 | 3 | | 3 | 170 | 13 |
| Oil 1 | 2 | 2 | 2 | 154 | 12 |
| Oil 2 | 3 | 3 | | 167 | 11 |
| Oil 2 | | 3 | 3 | 221 | 8 |
| Oil 2 | 3 | | 3 | 221 | 21 |
| Oil 2 | 2 | 2 | 2 | 270 | 10 |

The mixture wear data are interesting and unexpected. The first three pairs of bars in FIG. 1B show binary mixtures of the carbon blacks A, B, and C. The HFRR wear scars are not much different than the wear scars from single carbon blacks in FIG. 1A. However, the three-way mixture using about 2% each of carbon blacks A, B, and C dramatically increases the discrimination between Oils 1 and 2. The HFRR wear for Oil 1 (the good M-11EGR lubricant) is essentially unchanged but the wear scar for Oil 2 (the poor M-11EGR lubricant) is much worse, at least about 40% greater than the wear scar for single carbon blacks and about 20% greater than for the binary mixtures.

Figure 1B:
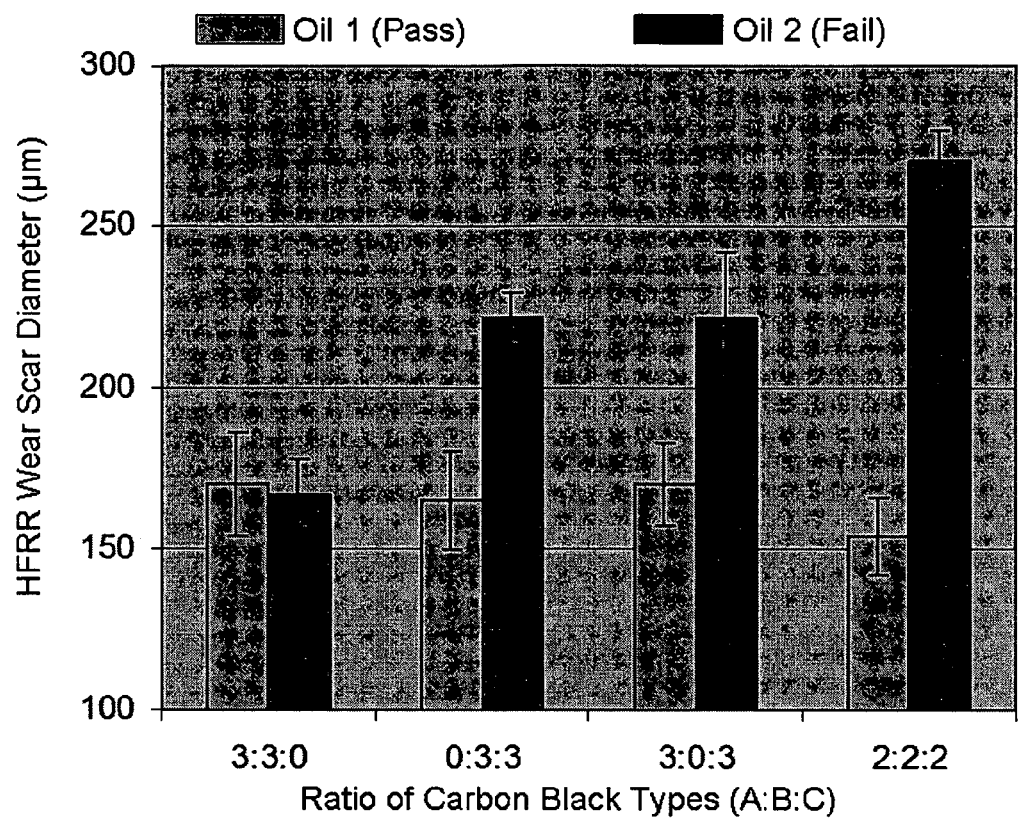
FIG. 1B illustrates the effect of carbon blacks of mixed particle size on HFRR wear data for mixtures of carbon blacks.

The standard deviation in the HFRR wear scars for the carbon black—lubricating oil mixtures are indicated as error bars in FIGS. 1A and 1B. In general, the error bars are about 10 to about 20 micrometers, representing one standard deviation in the wear tests. Since discrimination is usually the most important criterion for a bench test, the best option is to use the mixed particle size, i.e., about 2% by weight of each of the three carbon black components. Not only did the mixture of three carbon black components yield the best discrimination between the oils, but the standard deviations in the wear results were the lowest (about 10 or about 12 microns, depending upon the oil tested).

On the basis of these results, it is concluded that using three different carbon black components with similar surface chemistry but different particle size provided the least variable, most accurate correlation for wear performance between lubricating oils. The statistically designed mixture study shows that a mixture of three carbon black components in about equal proportion gave the optimum combination for HFRR wear discrimination and reduced the variability of the wear results. A mixture of three carbon black components in about equal proportion, each with different particle sizes, gave the best discrimination of wear performance for the Cummins M-11EGR reference oils (Oil 1 and Oil 2).

What is claimed is:

1. A method to determine the valve train wear performance of a lubricating oil, said method comprising adding to the lubricating oil from about 2% to about 9% by weight, based on the total weight of the lubricating oil, of a mixture of at least three independent carbon black components of mixed particle size and measuring the wear induced in a wear test.

2. The method according to claim 1, wherein the amount of the mixture of carbon black components is from about 5% to about 7% by weight, based on the total weight of lubricating oil.

3. The method according to claim 1, wherein the lubricating oil is a lubricating oil comprising a major amount of base oil of lubricating viscosity and minor amount of at least one additive selected from the group consisting of detergents, dispersants, oxidation inhibitors, rust inhibitors, demulsifiers, extreme pressure agents, friction modifiers, multifunctional additives, viscosity index improvers, pour point depressants, foam inhibitors and wear inhibitors.

4. The method according to claim 1, wherein the wear test is a high-frequency reciprocating rig test.

5. The method according to claim 1, wherein the particle size of each carbon black component is independently in the range from about 10 nanometers to about 100 nanometers.

6. The method according to claim 5, wherein the particle size of each carbon black component is independently in the range from about 10 nanometers to about 75 nanometers.

7. The method according to claim 6, wherein the particle size of each carbon black component is independently in the range from about 15 nanometers to about 60 nanometers.

8. The method according to claim 1, wherein the mixture of carbon black components is a mixture of three carbon black components.

9. The method according to claim 8, wherein the concentration of each carbon black component in the lubricating oil will independently range from about 1.8% to about 2.2% by weight, base on the total weight of the lubricating oil.

10. The method according to claim 9, wherein the concentration of each carbon black component in the lubricating oil is about 2% by weight, based on the total weight of the lubricating oil.

11. The method according to claim 10, wherein the three carbon black components have a particle size of 17 nanometers, 29 nanometers and 56 nanometers, respectively.

* * * * *